United States Patent
Hoescheler et al.

(10) Patent No.: US 7,098,259 B2
(45) Date of Patent: Aug. 29, 2006

(54) CATIONICALLY CURABLE DENTAL MATERIALS

(75) Inventors: Stefan Hoescheler, Herrsching (DE); Wolfgang Weinmann, Gilching (DE); Andrea Stippschild, Landsberg (DE); Susanne Wegner, Buchs (DE)

(73) Assignee: 3M ESPE AG, Seefeld (DE)

( * ) Notice: Subject to any disclaimer, the term of this patent is extended or adjusted under 35 U.S.C. 154(b) by 0 days.

(21) Appl. No.: 10/250,812

(22) PCT Filed: Jan. 8, 2002

(86) PCT No.: PCT/EP02/00101

§ 371 (c)(1),
(2), (4) Date: Sep. 23, 2003

(87) PCT Pub. No.: WO02/055028

PCT Pub. Date: Jul. 18, 2002

(65) Prior Publication Data

US 2004/0116550 A1    Jun. 17, 2004

(30) Foreign Application Priority Data

Jan. 9, 2001    (DE) ............................... 101 00 680

(51) Int. Cl.
*A61K 6/08* (2006.01)
*A61K 5/00* (2006.01)
*C08K 3/22* (2006.01)

(52) U.S. Cl. .................. 523/117; 523/116; 524/493; 106/35; 501/55; 433/228.1

(58) Field of Classification Search ............... 523/117, 523/116; 524/493; 106/35; 501/55
See application file for complete search history.

(56) References Cited

U.S. PATENT DOCUMENTS

| | | | |
|---|---|---|---|
| 4,220,461 A | 9/1980 | Samanta | |
| 4,503,169 A | 3/1985 | Randklev | |
| 4,714,721 A | 12/1987 | Franek et al. | |
| 4,764,497 A | 8/1988 | Yuasa et al. | |
| 5,176,747 A * | 1/1993 | Panzera et al. ............ 106/35 |
| 5,545,676 A | 8/1996 | Palazzotto et al. | |
| 5,641,347 A | 6/1997 | Grabowski et al. | |
| 5,856,373 A | 1/1999 | Kaisaki et al. | |
| 5,948,129 A * | 9/1999 | Nonami et al. ............ 65/33.1 |
| 6,084,004 A | 7/2000 | Weinmann et al. | |
| 6,136,737 A | 10/2000 | Todo et al. | |
| 6,270,348 B1 * | 8/2001 | Petersen ................ 433/228.1 |
| 6,297,181 B1 | 10/2001 | Kunert et al. | |
| 6,306,926 B1 * | 10/2001 | Bretscher et al. ........... 523/116 |
| 6,362,251 B1 | 3/2002 | Alkemper et al. | |
| 6,363,251 B1 * | 3/2002 | Huang et al. ............ 455/432.1 |

FOREIGN PATENT DOCUMENTS

| | | |
|---|---|---|
| DE | 34 21 155 A1 | 12/1985 |
| DE | 34 21 157 A1 | 12/1985 |
| DE | 44 43 173 A1 | 7/1996 |
| DE | 198 58 126 A1 | 6/1999 |
| DE | 198 49 388 A1 | 5/2000 |
| DE | 198 49 388 C2 | 5/2001 |
| EP | 0 634 373 A1 | 1/1995 |
| EP | 0 728 790 A1 | 8/1996 |
| EP | 0 897 710 A2 | 2/1999 |
| EP | 0 897 710 A3 | 2/1999 |
| EP | 0 728 790 B1 | 5/2000 |
| WO | WO 98/22521 A1 | 5/1998 |
| WO | WO 00/20494 A1 | 4/2000 |

OTHER PUBLICATIONS

Bowen et al., "121:18236p An esthetic glass-ceramic for use in composite restoration inserts" Chemical Abstracts, 1-Pharmacology, Weisberger, Ed., vol. 121, No. 15, 2 Publication pages. and pp. 1 and 562 (4 pp. total) (Oct. 10, 1994).
de Gee et al., "Occlusal wear stimulation with the ACTA wear machine," *Journal of Dentistry*, Butterworth-Heinemann Ltd., Oxford, UK, vol. 22, Suppl. No. 1, Title page, Publication page, Table of Contents, and pp. S21-S27 (9 pp. total) (1994).

(Continued)

*Primary Examiner*—Tae H. Yoon
(74) *Attorney, Agent, or Firm*—Mueting, Raasch & Gebhardt, P.A.

(57) ABSTRACT

The invention relates to a polymerizable dental material containing: (a) 3 to 80 wt. % of one or more cationically curable monomers; (b) 3 to 90 wt. % of one or more radio-opaque fillers; (c) 0.01 to 25 wt. % of initiators, retarders and/or accelerators, and; (d) 0 to 25 wt. % of auxiliary agents, whereby the cited percentages each refer to the total weight of the material. Filler (b) is produced by means of a melting method and is selected so that it has a refractive index of $n_D$=1.49–1.54, so that the viscosity of the polymerizable dental material, after a period of at least 9 months during which it was stored at a temperature ranging from 20 to 25° C., has a value of +/−50 % of the initial value measured 24 hours after the polymerizable dental material was produced, and so that the polymerizable dental material has a reactivity of the type that, once polymerization is initiated, the amount of the maximum heat flux generated by the dental material equals at least 0.8 mW/mg, and this maximum heat flux is attained within a period of no longer than 60s.

17 Claims, No Drawings

OTHER PUBLICATIONS

Harrysson et al., "Glass Formation in the System $Y_2O_3$-$Al_2O_3$-$SiO_2$ Under Conditions of Laser Melting," *Journal of European Ceramic Society*, Elsevier Science Limited, England, vol. 14, Title page, Publication page, Table of Contents, and pp. 377-381 (8 pp. total) (1994).

International Standard, ISO 4049, "Dentistry—Polymer-based filling, restorative and luting materials," Title page, Publication page, Table of Contents, Forward page, Introduction page, and pp. 1-27 (34 pp. total) (Jul. 15, 2000).

Billmeyer, Jr., Textbook of Polymer Science, Third Edition, John Wiley & Sons, New York, (1984), Title page, Publication page, and pp. 82-83 (4 pgs total).

Holleman-Wiberg, Inorganic Chemistry, Academic Press, San Diego, California, Title pages, Publication pages, and pp. 865-868 (translation—7 pgs total) (2001), and in German (1995) (Title page and pp. 923-925) (3 pgs total).

Scholze, Glass Nature, Structure, and Properties, Second revised Edition, Springer-Verlag, Berlin, Heidelberg, New York, (1977) (translation—5 pgs total), and in German (Title page and pp. 2-5) (3 pgs total).

Prassas, "Silica Glass from Aerogels," published on the Sol-gel Gateway: Glass from aerogels [online]. SolGel.com [retrieved on Feb. 4, 2005]. Retrieved from the Internet: <http://www.solgel.com/articles/april01/aerog3.htm>; 3 pgs.

* cited by examiner

CATIONICALLY CURABLE DENTAL MATERIALS

The present application is a U.S. National Stage Application of PCT/EP02/00101, filed 8 Jan. 2002. The application also claims the benefit under 35 U.S.C. §119 of foreign application no. DE 101 00 680.2, filed 9 Jan. 2001.

The invention relates to polymerizable dental materials based on cationically curable monomers and to a process for their preparation.

Polymerizable dental materials based on cationically curable monomers, such as, for example, plastic filling and fixing materials, are already known. In addition to a cationically curable monomer compound, they comprise an initiator system, suitable for starting the cationic polymerization, and fillers, as well as optionally retarders, accelerators and auxiliary agents. The monomers, together with the initiator system and optionally retarders, accelerators and auxiliary agents, is also known as matrix in which the fillers are incorporated.

Fillers which guarantee X-ray visibility of the dental materials are preferred. From a diagnostic viewpoint, it is advantageous if the usually tooth-colored dental material can be distinguished by X-ray diagnosis from the natural tooth substance. This means that the dental material should clearly be more difficult for X-rays to penetrate than the surrounding tooth substance.

In order to obtain in addition a particularly translucent dental material, use is preferably made of those fillers with a refractive index lying in the range of that of the matrix. These refractive indices are usually at $n_D=1.49–1.54$.

Known dental materials comprise, for example, quartz as filler. A good mechanical load-bearing capacity of the material can be produced using this. Quartz is of only limited suitability as sole filler for application in dental materials since the dental materials filled with it do not exhibit a satisfactory X-ray visibility. Quartz is particularly unsuitable where epoxides are used as matrix, since it has, at 1.55, a refractive index which is too high.

Polymerizable dental materials based on epoxides and their use as filling and fixing materials are disclosed in detail in WO 98/22521 A1. In this case, the polymerization shrinkage, which hitherto inevitably occurred with polymerizable dental materials based on acrylates and/or methacrylates, is particularly significant. Dental materials which, during polymerization, retain their exact shape or exhibit a shrinkage in volume of less than 1% are desirable.

A barium-free X-ray-opaque dental glass exhibiting an $SiO_2$ content of 20 to 45 weight % is disclosed in DE 198 49 388 A1 as possible filler. At least 65% of other oxides are correspondingly present in this filler. Owing to the maximum content of 10 weight % of $La_2O_3$ and 10 weight % of $ZrO_2$, the glass composition exhibits a relatively high content of basic and/or amphoteric oxides. These fillers are mainly used for the preparation of dental materials based on radically curable monomers. When such glasses are used as filler in cationically curable dental materials, the substance no longer satisfactorily cures or does not polymerize at all. The resulting dental material has only unsatisfactory mechanical strength values.

A dental glass visible by X-rays which is disclosed in EP 0 634 373 A1 comprises, for example, 15–35 weight % of SrO, 0–10 weight % of CaO, 5–20 weight % of $B_2O_3$, 5–20 weight % of $Al_2O_3$ and 45–65 weight % of $SiO_2$. The glasses prepared certainly exhibit good X-ray visibility. However, the excessively high content of $Al_2O_3$ and $B_2O_3$, together at least 10 weight %, is disadvantageous, as is the low storage stability of the dental materials prepared with this filler.

U.S. Pat. No. 4,764,497 discloses $SiO_2$-comprising fillers and their process of preparation. These fillers are prepared using a sol-gel process, in order to obtain a particle which is as spherical as possible. They are used, for example, to improve the mechanical properties and the surface properties of dental materials and to reinforce the substance. The incorporation of these fillers in radically curing acrylate or methacrylate matrices is revealed.

An X-ray-opaque cationically polymerizable composition with radio-opaque fillers is disclosed in WO 00/20494 A1. In addition to a cationically curable monomer compound, it comprises fillers and an initiator system suitable for starting the cationic polymerization. The fillers mentioned are chosen so that the Barcol hardness of the polymerized dental material reaches at least 10 units within 30 min. The dental materials with the fillers disclosed generally exhibit an unsatisfactory storage stability or too low a reactivity.

It was impossible to date, with the fillers known from the state of the art, to prepare storage-stable and simultaneously reactive dental materials based on the cationically curable monomers described here.

It is therefore the object of the present invention to make available a cationically curable X-ray-opaque dental material with a storage stability and reactivity corresponding to the general requirements.

This is achieved by a dental material including:

(a) 3 to 80 weight % of one or more cationically curable monomers, (b) 3 to 90 weight % of one or more X-ray-opaque fillers, (c) 0.01 to 25 weight % of initiators, retarders and/or accelerators, (d) 0 to 25 weight % of auxiliary agents, wherein the percentages are in each case with reference to the total weight of the material and wherein the filler (b) is prepared by a melting process and is chosen so that it exhibits a refractive index of $n_D=1.49–1.54$, and so that the values, measured according to method 4 (see Description to the Examples), of the viscosity determination of the polymerizable dental material, at a storage temperature of 20 to 25° C. over at least 9 months, does not exceed or fall below a value of +/−50% of the starting value, measured 24 h after preparation of the polymerizable dental material, and so that the polymerizable dental material exhibits a reactivity such that, after the start of polymerization, the amount of the maximum heat flux generated by the dental material, determined according to method 5 (see Description to the Examples), amounts to at least 0.8 mW/mg and this maximum heat flux is achieved within at most 60 s.

Such a dental material comprises one or more cationically curable monomers, and also initiators and optionally retarders, accelerators and/or auxiliary agents, which represent the "matrix". The filler or fillers are embedded in this matrix. The fillers have the job, when used in dental materials, of adjusting certain physical properties of the dental material. In the process, the proportion of filler can amount to 3–90 weight %. It is usually 20–90 weight %, particularly preferably 40–85 weight %.

The following requirements can be met using the dental materials according to the invention with the composition described:

X-Ray Visibility:

The X-ray visibility of dental fillers is given relative to the X-ray absorption of aluminum according to EN ISO 4049, Section 7.14. The materials claimed according to the present invention exhibit a relative aluminum X-ray equivalent of greater than 140%.

Appearance/Opacity:

In order to obtain dental materials with an appearance or translucency resembling that of the natural tooth substance, the refractive indices of matrix and fillers may differ only slightly from one another. Usually, the refractive indices ($n_D$) of both components should differ from one another by less than 0.05. The opacity, which should assume a value of 40–70% and is achieved by the dental materials according to the invention, is used to assess the esthetic properties.

Mechanical Load-Bearing Capacity:

The mechanical load-bearing capacity of a dental material and the abrasion resistance must be high enough for the dental material to be able to withstand for several years the stresses which occur on biting. The bending strength and the modulus of elasticity (EN ISO 4049), compressive strength, surface hardness and the two- or three-body abrasion (J. Dent., 1994, 22, Suppl. 1, pp. 21–7) above all are determined to determine the mechanical load-bearing capacity.

No cationically curable dental materials were hitherto known which comprised X-ray-visible fillers, satisfied the esthetic requirements and were both stable on storage as well as sufficiently reactive. The dental materials according to the invention meet these requirements. Surprisingly, it has been ascertained that, at the same time, good mechanical strength values can be achieved with these dental materials. The materials according to the invention exhibit a bending strength of more than 80 MPa.

The compounds disclosed in WO 98/22521 A1, WO 00/20494 A1 and EP 0 897 710 A2, oxetanes, vinyl ethers, spiro-orthoesters, spiro-orthocarbonates, bicyclic orthoesters, bicyclic monolactones, bicyclic bislactones, cyclic carbonates or combinations thereof, for example, are used as cationically curable monomers. It is likewise possible to use cationically curable monomers additionally exhibiting radically curing groups.

Initiators according to component (c) of the materials according to the invention can be: Lewis or Brönsted acids or compounds which release such acids, which initiate the polymerization, for example $BF_3$ or its ether adducts ($BF_3.THF$, $BF_3.Et_2O$, and the like), $AlCl_3$, $FeCl_3$, $HPF_6$, $HAsF_6$, $HSbF_6$ or $HBF_4$, or substances which trigger the polymerization after exposure to UV radiation or visible light or through heat and/or pressure, such as (η-6-cumene)(η-5-cyclopentadienyl)iron hexafluorophosphate, (η-6-cumene)(η-5-cyclopentadienyl)iron tetrafluoroborate, (η-6-cumene)(η-5-cyclopentadienyl) iron hexafluoroantimonate, substituted diaryliodonium salts and triarylsulfonium salts. Compound initiator systems, as disclosed in U.S. Pat. No. 6,084,004 or U.S. Pat. No. 5,545,676, may particularly preferably be used. In addition, combinations of the various constituents can be used as initiator system.

Condensed polyaromatics or peroxy compounds of the perester, diacyl peroxide, peroxydicarbonate and hydroperoxide type can be used as accelerators according to component (c). Hydroperoxides are preferably used; cumene hydroperoxide as an approximately 70 to 90% solution in cumene is particularly preferably used as accelerator. Bases, typically tertiary amines, can be added as retarders.

The component (c) is present in the dental material according to the invention in an amount of 0.01 to 25 weight %, preferably 0.01 to 20 weight %, with reference to the total weight of the material.

Suitable auxiliary agents according to component (d) can, for example, be conventional stabilizers, rheology modifiers, pigments and/or diluents used in the dental field.

The X-ray-opaque fillers according to component (b) are chosen from the group of the X-ray-visible glasses with a suitable refractive index. $SiO_2$ glasses comprising one or more oxides of the elements from the 5th and 6th period, such as Sr, Y, Zr, Nb, Ba, La, Hf or Ta, and/or one or more oxides of other heavy elements, such as Zn, Ga or Ge, are suitable for this. The oxides of the elements mentioned but also their carbonates, hydroxides, silicates, borates or other glass raw materials are suitable in principle for the preparation of the fillers (b). The calculation is carried out in spite of the raw materials used, always with respect to the oxide form.

It is a subject matter of the present invention that those glasses which are prepared by a melting process and are chosen so that they exhibit a refractive index of $n_D$=1.49–1.54 are used as fillers.

In addition, the dental materials according to the invention with the chosen fillers exhibit good stability on storage. This is shown by the values of the viscosity determination, measured according to method 4 (see Description to the Examples). These values are, at a storage temperature of 20 to 25° C. over at least 9 months, at most +/−50% of the starting value, measured 24 h after preparation of the polymerizable dental material.

It is particularly advantageous if the values of the viscosity determination, at a storage temperature of 20 to 25° C. over at least 15 months, do not exceed or fall below +/−50%, in particular +/−30%, of the starting value.

The reactivity of the polymerizable dental materials according to the invention with the filler according to component (b) is so high that, after the start of polymerization, the amount of the maximum heat flux generated by the dental material, determined according to method 5, amounts to at least 0.8 mW/mg and this maximum heat flux is achieved within at most 60 s.

The fillers according to component (b) are prepared in the following ways: A high temperature melting process is carried out, in which the presence of oxides suitable for favoring the melting properties of the glasses is not necessary. Such high temperature melting processes are, for example, induction melting processes. In these processes, the constituents of the filler are melted in a crucible, without the wall of the crucible coming into contact with the hot melt. This is achieved by heating the glass raw materials in an electric induction field. This produces a thermal gradient inside the crucible, so that the temperature necessary for the melting is reached only in the core. Normal melting temperatures are 1500–3000° C. Use of oxides which favor the melting properties is also unnecessary in plasma melting processes. In this connection, the glass raw materials are melted in an electric arc. Even higher temperatures than in the induction melting process can be achieved. A further advantage of some plasma melting processes is the very fast rates of cooling. Consequently, glasses which are very strongly inclined toward phase separation can also clearly be melted. It is particularly advantageous that the glass in some plasma melting processes is obtained already in a pulverulent form, so that the following grinding procedure becomes less expensive. Additional processes for high temperature melting are possible. These are, for example, various arc melting processes for oxide materials, such as are known from the preparation of $SiO_2$ glass and the melt-cast refractories for the glass industry. Additional high temperature melting processes are, e.g., laser melting, in which very high temperatures are achieved, as described in R. Harrysson: Glass Formation in the System $Y_2O_3$—$Al_2O_3$—$SiO_2$ under Conditions of Laser Melting.

The fillers currently claimed exhibit a liquidus temperature higher than 1500° C., preferably higher than 1600° C. In order to obtain a sufficiently low viscosity of the melt, temperatures of at least 50° C. above the liquidus temperature are necessary. This is why the claimed fillers relate to systems which are melted at a temperature of at least 1550° C., preferably 1650° C. At this temperature, comparatively high-viscosity melts are obtained. Melts of lower viscosity can also be prepared which exist at melting temperatures of 1600° C., preferably 1700° C.

Fillers which are suitable for use in the dental materials according to the invention preferably exhibit the following composition:

| Oxides | Proportion |
| --- | --- |
| $SiO_2$ | 65–95 weight % preferably 75–90 weight % |
| $Al_2O_3$, $B_2O_3$ and/or $P_2O_5$ | total 0–3 weight % preferably 0–1 weight % |
| MgO and/or CaO | total 0–10 weight % preferably 0–3 weight % |
| One or more of the oxides chosen from the group: $Li_2O$, $Na_2O$, $K_2O$, $Rb_2O$ and $Os_2O$ | total 0–3 weight % preferably 0–1 weight % |
| SrO and/or BaO | total 0–3 weight % preferably 0–2 weight % |
| One or more of the oxides chosen from the group $Y_2O_3$, $Ln_2O_3$, $ZrO_2$, $HfO_2$, $Nb_2O_5$, $Ta_2O_5$, $SnO_2$, $GeO_2$, $In_2O_3$ and $WO_3$ | total 5–35 weight % preferably 10–25 weight % | in which Ln represents an element from the lanthanide group (La—Lu) and in which both oxides free from water of crystallization and oxides comprising water of crystallization can be used.

The average particle size is determined using a laser particle sizer (Cilas). It is particularly advantageous to incorporate the fillers having an average particle size preferably of 0.6 to 3.0 μm, particularly preferably of 0.8 to 1.5 μm, and a specific surface (BET) preferably of 1–35 $m^2/g$, particularly preferably of 3–9 $m^2/g$.

These compositions represent fillers which have a refractive index suitable for the matrix and guarantee the X-ray visibility of the dental material.

Surprisingly, it has been established that the dental materials according to the invention exhibit the abovementioned advantages and in addition have a bending strength of at least 80 MPa. At the same time, cationically curing dental materials are thus obtained which have a suitable reactivity and simultaneously can be satisfactorily stored in the paste form.

The preparation of various glasses for use as fillers for polymerizable dental materials based on cationically curable monomers is described below with examples.

Table 1 shows the oxide composition of the various glasses. The glasses according to examples 1–23 are prepared using processes described below:

1. Glass Preparation

EXAMPLES 1–9 (MELTING PROCESSES)

Commercially available oxides, such as silicon dioxide, lanthanum oxide, zirconium oxide, yttrium oxide, calcium oxide, hafnium dioxide and tantalum oxide, are used as starting materials. The desired oxides are homogeneously mixed in accordance with the ratio desired in the glass composition. The powder obtained is then processed to a glass according to one of the melting processes described below:

a) Plasma Melting Process (Examples 1–2):

The powder obtained above is conveyed to a plasma melting unit and is melted at a temperature of 2000–3000° C.

b) Induction Melting Process (Examples 3–9):

The powder obtained from the mixture of oxides is melted in an inductively heated furnace at a temperature of 1550–2800° C. over a time of 5–60 min and is subsequently quenched in water.

Furthermore, additional melting processes, in which correspondingly high temperatures of at least 1550° C. are achieved, can also be employed instead of the plasma or induction melting processes described here. These are, for example, laser melting processes.

COMPARATIVE EXAMPLES 10–15 (SOL-GEL PROCESSES)

Organometallic compounds, such as tetraethyl orthosilicate, aluminum butoxide, zirconium propoxide, lanthanum ethoxide or calcium isopropoxide, are employed in the preparation of glass. The raw materials are dissolved in isopropanol and hydrolyzed by dropwise addition of water. After stirring for several hours, the solutions gel and, after filtering off, are dried in a drying cabinet at 150° C. for approximately 24 h and are subsequently ground up in a mortar. The powder obtained is calcined at a temperature of 800–1050° C. for 2 h.

COMPARATIVE EXAMPLES 16–17 (SOL-GEL PROCESSES)

Comparative examples 16 and 17 are taken from the state of the art. The preparation is described on page 67 and page 69 of WO 00/20494 A1 under "Example 25" or "Example 33".

COMPARATIVE EXAMPLES 18–26 (MELTING PROCESSES)

With the use of glass raw materials, such as quartz powder, aluminum hydroxide, mullite, sodium carbonate, boric acid, zirconium oxide, lanthanum oxide, yttrium oxide, calcium hydroxide, magnesium oxide or lithium carbonate, glasses are melted according to conventional processes in a platinum crucible at a temperature of 1400 to 1500° C. over a time of 2–4 h and are subsequently quenched in water. Various raw materials, such as carbonates, hydroxides, oxides and silicates, can in principle be used in the preparation of glass.

COMPARATIVE EXAMPLES 27–29 (MELTING PROCESSES)

Comparative examples 27 to 29 are produced according to the processes disclosed in WO 00/20494. They are listed there as "Example 6", "Example 11" and "Example 16".

COMPARATIVE EXAMPLE 30

The filler consists of a commercially available fumed $SiO_2$ (Aerosil® OX 50, Degussa).

COMPARATIVE EXAMPLE 31

Comparative example 31 represents a commercially available quartz (Quarzwerke Frechen).

fine milling is in the case of all glass powders subsequently carried out in an attrition mill lined with aluminum oxide, with zirconium oxide milling balls 0.8 mm in size. Water is used as grinding medium.

Two pastes with different particle size distributions are in each case prepared from the glasses 18 to 21. For that, the glasses of examples 18 to 21 are used as starting material for two different grinding processes. The glasses of examples 18 to 21 are both premilled and finely milled, according to the abovedescribed processes, for the processing to the pastes P 24, P 26, P 28 and P 30. The glasses of examples 18 to 21 are used without premilling for the processing to the pastes P 25, P 27, P 29 and P 31. In this connection, only a premilling with a swing mill over a longer period of time (60 min) is carried out, without subsequent fine milling. The resulting average particle size is coarser.

TABLE 1

Composition of the fillers 1–31 in weight %

| | Ex. | | | | | | | | | | | | | | | | |
|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 |
| $SiO_2$ | 85 | 80 | 80 | 77 | 83 | 88 | 79 | 83 | 85 | 85 | 58 | 80 | 75 | 47 | 68 | 66 | 80.6 |
| $B_2O_3$ | | | | | | | | | | | | | | | | | 3 |
| $Al_2O_3$ | | | | 3 | | | | | | | | | 16 | 53 | 14 | | |
| $Li_2O$ | | | | | | | | | | | | | | | | | |
| $Na_2O$ | | | | | | | | | 1 | | | | | | | | |
| CaO | | | | | | | 4 | | | | | | 9 | | | | |
| MgO | | | | | | | | | 1 | | | | | | | | |
| SrO | | | | | | | | | | | | | | | | | |
| BaO | | | | | | | | | | | | | | | | | |
| $Y_2O_3$ | | | | | 4 | | | 5 | | | | | | | | | |
| $La_2O_3$ | | 10 | 10 | 10 | | | | | 1 | | | 10 | | | | 34 | 16.4 |
| $ZrO_2$ | | 10 | 10 | | 14 | 8 | | 8 | 12 | 15 | 26 | 10 | | | 18 | | |
| $TiO_2$ | | | | | | | | | | | | 16 | | | | | |
| $HfO_2$ | 15 | | | 13 | | | | | | | | | | | | | |
| $Ta_2O_5$ | | | | | | | 21 | | | | | | | | | | |

| | Ex. | | | | | | | | | | | | | |
|---|---|---|---|---|---|---|---|---|---|---|---|---|---|---|
| | 18 | 19 | 20 | 21 | 22 | 23 | 24 | 25 | 26 | 27 | 28 | 29 | 30 | 31 |
| $SiO_2$ | 73 | 77 | 62 | 76 | 57 | 70 | 72 | 46 | 73 | 55 | 30 | 52 | 99.9 | 99.9 |
| $B_2O_3$ | | | 10 | 11 | 16 | | | | | 10 | 30 | | | |
| $Al_2O_3$ | 3 | | 7 | 5 | | 20 | 3 | 39 | 13 | 10 | 10 | 35.7 | | |
| $Li_2O$ | | | | | | | | | 3 | | | | | |
| $Na_2O$ | 5 | 8 | | 5 | | | 15 | | | | | | | |
| CaO | | | | | | 10 | 10 | | | | | | | |
| MgO | | | | | | | | 15 | | | | | | |
| SrO | 16 | | 21 | 3 | | | | | | | | | | |
| BaO | | | | | | | | | | | 25 | | | |
| $Y_2O_3$ | | | | | | | | | 11 | | | | | |
| $La_2O_3$ | | | | | 27 | | | | | | | 12.3 | | |
| $ZrO_2$ | 3 | 15 | | | | | | | | | | | | |
| $TiO_2$ | | | | | | | | | | | | | | |
| $HfO_2$ | | | | | | | | | | | | | | |
| $Ta_2O_5$ | | | | | | | | | | | 30 | | | |

2. Grinding Procedure:

The glass powders obtained according to the abovedescribed examples 1–31 are, with the exception of the plasma-melted glasses (examples 1 and 2) and the fumed $SiO_2$ described in example 30, ground to a suitable average particle size using conventional grinding processes.

The premilling of the glass powders to an average particle size of 10–50 μm is carried out in a swing mill (Sliebtechnik; milling time 10–15 min). In the plasma-melted samples, glass granules with an average particle size of approximately 50 μm are already obtained using the melting process, so that here the working step of the premilling can be omitted. The The refractive indices of the individual fillers of table 1 are given in the following table 2. To determine the refractive indices, the glass powders to be investigated are added to liquids with known refractive indices. The refractive index of the respective filler can thus be exactly measured using a light microscope.

TABLE 2

| Example | Refractive index |
|---|---|
| 1 | 1.530 |
| 2 | 1.527 |

TABLE 2-continued

| Example | Refractive index |
|---|---|
| 3 | 1.528 |
| 4 | 1.526 |
| 5 | 1.514 |
| 6 | 1.511 |
| 7 | 1.539 |
| 8 | 1.525 |
| 9 | 1.502 |
| 10 | 1.529 |
| 11 | 1.72 |
| 12 | 1.529 |
| 13 | 1.491 |
| 14 | 1.484 |
| 15 | 1.549 |
| 16 | 1.522 |
| 17 | 1.505 |
| 18 | 1.518 |
| 19 | 1.538 |
| 20 | 1.513 |
| 21 | 1.481 |
| 22 | 1.55 |
| 23 | 1.481 |
| 24 | 1.504 |
| 25 | 1.540 |
| 26 | 1.527 |
| 27 | 1.528 |
| 28 | 1.514 |
| 29 | 1.528 |
| 30 | 1.465 |
| 31 | 1.545 |

3. Surface Treatment:

The glass powders are silanized in acetone solution to render the processing simpler. In all examples, glycidyloxypropyltrimethoxysilane is employed. The following silane concentrations in weight %, with reference to the filler, are used:

| example 1–29, 31 | 3 weight % |
| example 24–27 | 1 weight % |
| example 30 | 6 weight % |

Additional methods for surface treatment can likewise be envisaged.

4. Processing to Dental Materials:

After suitable surface treatment, the fillers are incorporated, using a standard kneader, in a monomer matrix to prepare dental materials. The monomer matrix exhibits, for example, one of the following compositions:

matrix 1:

| 14.53 weight % | di(3-epoxycyclohexylethyl)methylphenylsilane |
| 14.53 weight % | 1,3,5,7-tetrakis(2,1-ethanediyl-3,4-epoxycyclohexyl)-1,3,5,7-tetramethyltetraethylsiloxane |
| 0.30 weight % | Camphorquinone |
| 0.10 weight % | ethyl 4-dimethylaminobenzoate |
| 0.54 weight % | (4-methylphenyl)(4-isopropylphenyl)iodonium tetrakis(pentafluorophenyl)borate |
| 70.00 weight % | filler | matrix 2:

| 19.10 weight % | di(3-epoxycyclohexylethyl)methylphenylsilane |
| 9.50 weight % | 1,3,5,7-tetrakis(2,1-ethanediyl-3,4-epoxycyclohexyl)-1,3,5,7-tetramethyltetraethylsiloxane |
| 0.40 weight % | Camphorquinone |
| 0.15 weight % | ethyl 4-dimethylaminobenzoate |
| 0.72 weight % | (4-methylphenyl)(4-isopropylphenyl)iodonium tetrakis(pentafluorophenyl)borate |
| 70.13 weight % | filler | matrix 3:

| 12.42 weight % | di(3-epoxycyclohexylethyl)methylphenylsilane |
| 16.10 weight % | 1,3,5,7-tetrakis(2,1-ethanediyl-3,4-epoxycyclohexyl)-1,3,5,7-tetramethyltetraethylsiloxane |
| 0.35 weight % | Camphorquinone |
| 0.12 weight % | ethyl 4-dimethylaminobenzoate |
| 0.80 weight % | (4-methylphenyl)(4-isopropylphenyl)iodonium tetrakis(pentafluorophenyl)borate |
| 70.21 weight % | filler | matrix 4:

| 35.5 weight % | di(3-epoxycyclohexylethyl)methylphenylsilane |
| 35.5 weight % | 1,3,5,7-tetrakis(2,1-ethanediyl-3,4-epoxycyclohexyl)-1,3,5,7-tetramethyltetraethylsiloxane |
| 0.90 weight % | Camphorquinone |
| 0.25 weight % | ethyl 4-dimethylaminobenzoate |
| 0.45 weight % | (4-methylphenyl)(4-isopropylphenyl)iodonium tetrakis(pentafluorophenyl)borate |
| 27.40 weight % | filler |

The characterization of the pastes is carried out with regard to the following test criteria, summarized in table 3:

Opacity (Method 1)

The opacity is determined on samples with a thickness of 3.6 mm. For this, small sample plaques are prepared and are polymerized on each side for 40 s with a light polymerization apparatus (Elipar®, ESPE). The opacity measurement is carried out on a standard measurement apparatus (Labscan, CieLab).

Polymerization Depth (Method 2)

Test specimens are prepared in a cylindrical sample shape (height 12 mm, diameter 7 mm) and are illuminated on one side for 40 s with a light polymerization apparatus (Elipar®, ESPE). After illuminating, the unpolymerized parts are cut off with a knife from the cylinder on the side turned away from the light. The remaining length of cylinder, which consists of cured dental material which cannot be cut, describes the polymerization depth.

Three-Point Bending Strength (Method 3)

Three-point bending strength according to EN ISO 4049: The bending strength is determined according to EN ISO 4049 on 2×2×25 mm rods. It is used as measurement for satisfactory polymerization. A bending strength of 80 MPa, preferably 100 MPa, should be achievable for use as dental material.

Storage Stability (Method 4)

The storage stability is determined by the viscosity measurement via the deformation of an unpolymerized ball of dental material. For that, a ball of paste with a mass of 0.4 g is prepared. The ball, between two sheets, is placed under a load weighing 1575 g for 60 s and the height of the deformed test specimen is subsequently measured. The starting value, measured 24 h after preparing the dental material, the value at 9 months and the value at 15 months is used to assess the storage stability. Materials with a measured value after 9 months which does not exceed or fall below the starting value by more than 50% are regarded as stable on storage.

X-Ray Opacity:

The X-ray visibility is measured relative to the X-ray absorption of aluminum according to EN ISO 4049, Section 7.14.

The properties of the various dental materials prepared according to the compositions according to the invention are shown in the following table 3, in comparison with those dental materials comprising fillers known from the state of the art.

In table 3:
"Cured" means cured during storage
"n.c." means no cure (no curing possible)

polymerization, a reactivity which is too low (e.g., P27, P29). The reactivity of the materials is determined by photo DSC measurement. For this, approximately 30 mg of the material are illuminated in a DSC measurement apparatus (Netzsch DSC 200 cell) with a polymerization lamp (Elipar, ESPE Dental AG) for 40 s and the heat flux is followed over time from the beginning of illumination. Reactive materials in the sense of the present invention are present if the

TABLE 3

| Paste/Example | Filler | Matrix | Al X-ray equivalent [%] | Average particle size [μm] | Opacity [%] | Polymerization depth [mm] | Bending strength [MPa] | Storage stability Starting value [mm] | Storage stability 9 months [mm] | Storage stability 15 months [mm] |
|---|---|---|---|---|---|---|---|---|---|---|
| P 1  | 1  | 1 | 280 | 1.0 | 65 | 7    | 110  | 1.2 | 1.3   | 1.4 |
| P 2  | 1  | 2 | 280 | 1.0 | 66 | 7    | 128  | 1.3 | 1.4   | 1.5 |
| P 3  | 2  | 1 | 200 | 1.1 | 50 | 8    | 132  | 1.4 | 1.5   | 1.6 |
| P 4  | 2  | 2 | 200 | 1.1 | 64 | 7    | 98   | 1.3 | 1.3   | 1.5 |
| P 5  | 3  | 1 | 200 | 1.0 | 50 | 10   | 112  | 1.3 | 1.4   | 1.4 |
| P 6  | 3  | 2 | 200 | 1.0 | 61 | 7    | 98   | 1.2 | 1.3   | 1.4 |
| P 7  | 4  | 1 | 200 | 1.3 | 50 | 9    | 130  | 1.2 | 1.3   | 1.5 |
| P 8  | 4  | 2 | 200 | 1.3 | 62 | 7    | 110  | 1.4 | 1.5   | 1.7 |
| P 9  | 5  | 3 | 160 | 1.2 | 50 | 10   | 118  | 1.3 | 1.4   | 1.6 |
| P 10 | 6  | 2 | 210 | 1.0 | 60 | 7    | 102  | 1.2 | 1.2   | 1.4 |
| P 11 | 6  | 3 | 210 | 1.0 | 50 | 8    | 117  | 1.2 | 1.3   | 1.4 |
| P 12 | 7  | 2 | 240 | 1.3 | 51 | 10   | 124  | 1.4 | 1.5   | 1.7 |
| P 13 | 8  | 1 | 220 | 1.2 | 54 | 8    | 108  | 1.4 | 1.6   | 1.7 |
| P 14 | 8  | 2 | 220 | 1.2 | 62 | 7    | 105  | 1.4 | 1.7   | 1.8 |
| P 15 | 9  | 3 | 220 | 1.0 | 57 | 7    | 94   | 1.0 | 1.0   | 1.1 |
| P 16 | 10 | 1 | 220 | 1.0 | 50 | 9    | 140  | 1.3 | 2.3   | 2.9 |
| P 17 | 11 | 1 | 360 | 1.2 | 85 | 1.5  | 123  | 1.2 | 2.3   | 2.8 |
| P 18 | 12 | 1 | 200 | 1.2 | 50 | 9    | 112  | 1.3 | 2.0   | 3.0 |
| P 19 | 13 | 1 | 80  | 1.4 | 65 | 2    | 87   | 1.4 | 3.6   | 4.5 |
| P 20 | 14 | 1 | 80  | 1.2 | 65 | 3    | 102  | 1.5 | Cured | Cured |
| P 21 | 15 | 1 | 140 | 1.3 | 65 | n.c. | n.c. | 1.4 | 1.5   | Cured |
| P 22 | 16 | 1 | 220 | 1.4 | 55 | 8    | 110  | 1.8 | 4.0   | Cured |
| P 23 | 17 | 1 | 130 | 1.5 | 70 | 5    | 105  | 1.6 | Cured | Cured |
| P 24 | 18 | 1 | 180 | 1   | 50 | n.c. | n.c. | 1.3 | 1.4   | 1.4 |
| P 25 | 18 | 1 | 180 | 5.2 | 50 | 3    | 40   | 1.1 | 1.3   | 1.4 |
| P 26 | 19 | 1 | 220 | 1.3 | 60 | n.c. | n.c. | 1.0 | 1.1   | 1.1 |
| P 27 | 19 | 1 | 220 | 3.4 | 50 | 2    | 54   | 1.0 | 1.0   | 1.1 |
| P 28 | 20 | 1 | 200 | 0.9 | 50 | 1    | 60   | 1.8 | 3.3   | 3.5 |
| P 29 | 20 | 1 | 200 | 5.3 | 50 | 4    | 35   | 1.6 | 1.6   | 1.8 |
| P 30 | 21 | 1 | 80  | 1.4 | 80 | n.c. | n.c. | 1.4 | 3.7   | 4 |
| P 31 | 21 | 1 | 80  | 3.8 | 60 | 2    | 56   | 1.3 | 2.0   | 4 |
| P 32 | 22 | 1 | 200 | 1.3 | 80 | 3.5  | 125  | 1.5 | Cured | Cured |
| P 33 | 23 | 1 | 80  | 1.0 | 75 | 2    | 90   | 1.8 | 3.8   | 4 |
| P 34 | 24 | 1 | 80  | 0.9 | 65 | n.c. | n.c. | 1.0 | 1.0   | 1.1 |
| P 35 | 25 | 1 | 70  | 1.4 | 65 | 1.5  | 80   | 1.6 | Cured | Cured |
| P 36 | 26 | 1 | 140 | 1.1 | 50 | 3    | 103  | 1.8 | 4     | Cured |
| P 37 | 27 | 1 | 180 | 1.3 | 50 | 7    | 98   | 1.9 | Cured | Cured |
| P 38 | 28 | 1 | 300 | 1.4 | 65 | 6    | 120  | 1.8 | 3.5   | Cured |
| P 39 | 29 | 1 | 100 | 1.3 | 55 | 7    | 106  | 1.7 | Cured | Cured |
| P 40 | 29 | 1 | 80  | —   | 75 | 4    | 105  | 1.2 | Cured | Cured |
| P 41 | 30 | 4 | 60  | —   | 88 | 1    | 68   | 2.1 | Cured | Cured |
| P 42 | 31 | 2 | 60  | 1.3 | 80 | 3    | 122  | 1.0 | 1.1   | 1.2 |

It can be seen that the dental materials P1–P15 according to the invention, in comparison with the dental materials P16–P42 known from the state of the art, clearly exhibit better values for the storage stability. Quartz and fumed silica as fillers (P41, P42) are not X-ray-visible.

Reactivity (Method 5):

Dental materials have to be able to be processed and used in a short time. This applies in particular for filling materials which are cured with light and are supposed to be able to bear mechanical loads immediately after clinical care. As emerges from table 4, success is achieved in this respect with the reactive materials according to the invention (example P1–P15) which are provided with the suitable fillers. The fillers known from the state of the art which lead to dental materials which are stable on storage show, in the cationic amount of the heat flux generated by the material is at least 0.8 mW/mg and the maximum heat flux is achieved within at most 60 s.

TABLE 4

| Paste No. | Amount of the maximum heat flux [mW/mg] | Amount of the maximum heat flux is achieved after [s] |
|---|---|---|
| P 1  | 1.8 | 21 |
| P 3  | 1.9 | 18 |
| P 6  | 1.5 | 20 |
| P 7  | 2.1 | 16 |
| P 15 | 1.1 | 34 |

TABLE 4-continued

| Paste No. | Amount of the maximum heat flux [mW/mg] | Amount of the maximum heat flux is achieved after [s] |
|---|---|---|
| P 27 | 0.4 | 50 |
| P 29 | 0.6 | 72 |

What is claimed is:

1. A process for the preparation of a polymerizable dental material, the process comprising:
 (a) preparing a filler from individual components by a melting process at a temperature of at least 1550° C.;
 (b) grinding the filler obtained in (a) to a particle size of 0.1–15μm;
 (c) surface-treating the filler obtained in (b); and
 (d) incorporating the surface-treated filler in a matrix comprising:
  (i) cationically curable monomers; and
  (ii) initiators, retarders, accelerators, auxiliary agents, or combinations thereof; wherein the filler is an X-ray opaque filler comprising at least 65 weight % of $SiO_2$, and wherein the surface-treated filler has a refractive index of $n_D$=1.49–1.54.

2. The process of claim 1, wherein the melting process is carried out at a temperature of at least 1600° C.

3. The process of claim 1, wherein the melting process is carried out in an inductively heated furnace at 1550–3000° C. over 5 to 60 minutes, or in a plasma melting unit at 2000–3000° C.

4. The process of claim 1, wherein the polymerizable dental material comprises:
 (a) 3 to 80 weight % of one or more cationically curable monomers;
 (b) 3 to 90 weight % of the surface-treated filler;
 (c) 0.01 to 25 weight % of initiators, retarders and/or accelerators; and
 (d) 0 to 25 weight % of auxiliary agents;
wherein the percentages are in each case with reference to the total weight of the material;
wherein the filler (b) exhibits a refractive index of $n_D$=1.49–1.54;
wherein the polymerizable dental material, at a storage temperature of 20 to 25° C. for at least 9 months, has a viscosity of +/−50% of the starting value, which is measured 24 hours after preparation of the polymerizable dental material; and
wherein the polymerizable dental material has a reactivity such that, after the start of polymerization, the material generates a maximum heat flux of at least 0.8 mW/mg within at most 60 seconds.

5. The process of claim 1, wherein the polymerizable dental material is a dental bonding material.

6. The process of claim 1, wherein the polymerizable dental material is a dental fixing material.

7. The process of claim 1, wherein the surface-treated filler has an X-ray opacity corresponding to an aluminum X-ray equivalent of at least 100%.

8. The process of claim 1, wherein the surface-treated filler has a refractive index of $n_D$=1.50–1.53.

9. The process of claim 1, wherein the surface-treated filler has an average particle size of 0.1–15 μm and a specific surface of 1–35 $m^2$/g.

10. The process of claim 9, wherein the surface-treated filler has an average particle size of 1–4 μm and a specific surface of 3–9 $m^2$/g.

11. The process of claim 1, wherein the surface-treated filler comprises a total of at most 35 weight % of one or more of the oxides of the elements from the $5^{th}$ period, $6^{th}$ period, or both; a total of at most 3 weight % of one or more of the oxides from the first main group; and a total of at most 3 weight % of the oxides $B_2O_3$, $Al_2O_3$, and $P_2O_5$.

12. The process of claim 1, wherein the surface treated filler comprises a total of at most 35 weight % of one or more of the oxides chosen from the group consisting of $Y_2O_3$, lanthanide oxides, $ZrO_2$, $HfO_2$, $Nb_2O_5$, $Ta_2O_5$, $In_2O_3$, $SnO_2$, and $WO_3$; a total of at most 3 weight % of one or more of the oxides from the first main group; and a total of at most 3 weight % of the oxides $B_2O_3$, $Al_2O_3$, and $P_2O_5$.

13. The process of claim 1, wherein the polymerizable dental material comprises:
 (a) 3 to 80 weight % of one or more cationically curable monomers;
 (b) 3 to 90 weight % of one or more X-ray-opaque fillers;
 (c) 0.01 to 25 weight % of initiators, retarders, accelerators, or combinations thereof; and
 (d) 0 to 25 weight % of auxiliary agents;
wherein the percentages are in each case with reference to the total weight of the material.

14. The process of claim 1, wherein the polymerizable dental material, at a storage temperature of 20 to 25° C. for at least 9 months, has a viscosity of +/−50% of the starting value, which is measured 24 hours after preparation of the polymerizable dental material.

15. The process of claim 1, wherein the polymerizable dental material has a reactivity such that, after the start of polymerization, the material generates a maximum heat flux of at least 0.8 mW/mg within at most 60 seconds.

16. The process of claim 4, wherein the melting process is carried out at a temperature of at least 1600° C.

17. The process of claim 4, wherein the melting process is carried out in an inductively heated furnace at 1550–3000° C. over 5 to 60 minutes, or in a plasma melting unit at 2000–3000° C.

* * * * *

UNITED STATES PATENT AND TRADEMARK OFFICE
CERTIFICATE OF CORRECTION

| | |
|---|---|
| PATENT NO. | : 7,098,259 B2 |
| APPLICATION NO. | : 10/250812 |
| DATED | : August 29, 2006 |
| INVENTOR(S) | : Hoescheler et al. |

It is certified that error appears in the above-identified patent and that said Letters Patent is hereby corrected as shown below:

In column 8, Table 1, in the column for Ex. 7 and the row for $Ta_2O_5$, insert --21--;

In column 8, Table 1, in the column fro Ex. 8 and the row for $Ta_2O_5$, delete "21";

In column 14, line 21, Claim 12, delete "surface treated" and insert --surface-treated--.

Signed and Sealed this

Eighteenth Day of September, 2007

JON W. DUDAS
*Director of the United States Patent and Trademark Office*